(12) United States Patent
Klebuc et al.

(10) Patent No.: US 8,808,372 B2
(45) Date of Patent: Aug. 19, 2014

(54) BREAST IMPLANT SPACERS FOR THE TREATMENT OF PERIPROSTHETIC BREAST IMPLANT INFECTIONS

(75) Inventors: Michael Klebuc, Houston, TX (US); Elizabeth Ann Welter, Houston, TX (US)

(73) Assignee: Cold Winter Solutions, L.L.C., Houston, TX (US)

( * ) Notice: Subject to any disclaimer, the term of this patent is extended or adjusted under 35 U.S.C. 154(b) by 249 days.

(21) Appl. No.: 13/458,647

(22) Filed: Apr. 27, 2012

(65) Prior Publication Data

US 2013/0289721 A1    Oct. 31, 2013

(51) Int. Cl.
*A61F 2/12*    (2006.01)

(52) U.S. Cl.
USPC .......................................... 623/8

(58) Field of Classification Search
USPC ....................................... 623/7–8
See application file for complete search history.

(56) References Cited

U.S. PATENT DOCUMENTS

| | | | |
|---|---|---|---|
| 4,298,997 A | 11/1981 | Rybka | |
| 4,846,844 A | 7/1989 | DeLeon et al. | |
| 4,952,419 A | 8/1990 | DeLeon et al. | |
| 5,133,771 A | 7/1992 | Duncan et al. | |
| 5,618,286 A | 4/1997 | Brinker | |
| 6,155,812 A | 12/2000 | Smith et al. | |
| 6,361,731 B1 | 3/2002 | Smith et al. | |
| 6,942,475 B2 | 9/2005 | Ensign et al. | |
| 7,427,296 B2 | 9/2008 | Evans | |
| 7,429,346 B2 | 9/2008 | Ensign et al. | |
| 7,637,729 B2 | 12/2009 | Hartman et al. | |
| 7,842,095 B2 | 11/2010 | Klein | |
| 7,867,426 B2 | 1/2011 | Ziran et al. | |
| 2009/0216323 A1* | 8/2009 | Ledergerber | 623/8 |
| 2010/0168808 A1 | 7/2010 | Citron | |
| 2010/0198350 A1 | 8/2010 | Berg et al. | |
| 2011/0009960 A1* | 1/2011 | Altman et al. | 623/8 |
| 2011/0082545 A1 | 4/2011 | Freund | |
| 2011/0082546 A1* | 4/2011 | Freund | 623/8 |
| 2011/0106248 A1 | 5/2011 | Kokott et al. | |
| 2011/0137244 A1* | 6/2011 | Lee et al. | 604/103.02 |
| 2011/0137412 A1 | 6/2011 | Nyte | |
| 2011/0153017 A1 | 6/2011 | McClellan | |
| 2011/0160854 A1* | 6/2011 | Berg et al. | 623/8 |
| 2011/0262511 A1 | 10/2011 | Love et al. | |
| 2012/0052292 A1* | 3/2012 | Pulapura et al. | 428/336 |
| 2012/0221105 A1* | 8/2012 | Altman et al. | 623/8 |
| 2012/0253460 A1* | 10/2012 | Ledergerber | 623/8 |
| 2014/0039617 A1* | 2/2014 | Maxwell | 623/8 |

FOREIGN PATENT DOCUMENTS

GB    2040688 A    9/1980

OTHER PUBLICATIONS

Bennett, et al., "Management of exposed, infected implant-based breast reconstruction and strategies for salvage," J. Plast. Reconstr. Aesthet. Surg. 64:1270-1277, 2011.
Courtiss, et al., "The fate of breast implants with infections around them," Plast. Reconstr. Surg. 63:812-816, 1979.
Cui, et al., "Antibiotic-impregnated cement spacers for the treatment of infection associated with total hip or knee arthroplasty," J. Bone Joint Surg. Am. 89:871-872, 2007.

(Continued)

*Primary Examiner* — Suzette J Gherbi
(74) *Attorney, Agent, or Firm* — Vinson & Elkins LLP (57) ABSTRACT

The present disclosure provides improved devices and methods to treat periprosthetic breast implant infections.

38 Claims, 5 Drawing Sheets

(56) References Cited

OTHER PUBLICATIONS

Diefenbeck, et al., "Prophylaxis and treatment of implant-related infections by local application of antibiotics," Injury 37:S95-S104, 2006.
Feldman, et al., "Breast implant infections: Is cefazolin enough?" Plast. Reconstr. Surg. 126:779-785, 2010.
Freedman and Jackson, "Infections in breast implants," Infect. Dis. Clin. North Am. 3:275-287, 1989.
Lapid, "Use of gentamicin collagen sponges for the treatment of periprosthetic breast implant infection," J. Plast. Reconstr. Aesthet. Surg. 64:e313-e316, 2011.
Spear, et al., "The infected of exposed breast implant: Management and treatment strategies," Plast. Reconstr. Surg. 113:1634-1644, 2004.
Spear, et al., "Management of the infected or exposed breast prosthesis: A single surgeon's 15-year experience with 69 patients," Plast. Reconstr. Surg. 125:1074-1084, 2010.
Yii and Khoo, Salvage of infected expander prostheses in breast reconstruction, Plast. Reconstr. Surg. 111:1087-1092, 2003.
Invitation to Pay Additional Fees and Partial International Search Report, International Patent Application No. PCT/US2013/037064, Aug. 5, 2013.

* cited by examiner

BREAST IMPLANT SPACERS FOR THE TREATMENT OF PERIPROSTHETIC BREAST IMPLANT INFECTIONS

CROSS-REFERENCE TO RELATED APPLICATION

Not Applicable.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present disclosure generally concerns devices and methods for the treatment of infections arising from breast implants.

2. Description of the Related Art

Approximately one in nine women in the United States are diagnosed with breast cancer each year, and approximately 90,000 women per year choose to undergo breast reconstruction utilizing tissue expansion followed by insertion of a permanent breast implant. Unfortunately, approximately 20-24% of these reconstructions will be complicated by development of a periprosthetic implant infection. In addition, in the year 2010 approximately 270,000 women underwent cosmetic breast augmentation, and approximately 2.0-2.5% are expected to develop a periprosthetic implant infection. Periprosthetic infection of an expander-implant breast reconstruction or augmented breast is considered a devastating complication.

A number of recent protocols have been described to attempt to prevent infection in conjunction with the initial breast implant procedure. Such protocols include extensive irrigation of the implant location with antibiotics during the implant procedure (United States Patent Application Publication No. US 2011/0137412 A1), coating the implant with antibiotics (United States Patent Application Publication No. US 2010/0198350 A1; United States Patent Application Publication No. US 2011/0106248 A1; United States Patent Application Publication No. US 2011/0262511 A1), and using implants that are surrounded by an antibiotic-eluting pocket (United States Patent Application Publication No. US 2011/0160854 A1) or biodegradable mesh (United States Patent Application Publication No. US 2010/0168808 A1; United States Patent Application Publication No. US 2011/0082545 A1). Additionally, in cases of reconstructive breast implantation, treatment with antibiotics during tissue expansion (United States Patent Application Publication No. US 2011/0137244 A1). However, even though such protocols can reduce the incidence of periprosthetic breast implant infections, they are not 100% effective.

Initial attempts to treat periprosthetic breast implant infections using antibiotics alone were somewhat effective, but was associated with development of a hard, painful reconstructed breast (symptomatic capsular contracture) in up to 68% of cases (Courtiss, et al., Plast. Reconstr. Surg. 63:812-816, 2003).

Current treatment protocols for periprosthetic breast implant infections employ the use of oral and intravenous antibiotic therapy often followed by surgical debridement and implant exchange, also known as implant salvage (Yii and Khoo, Plast. Reconstr. Surg. 111:1087-1092, 2003; Spear, et al., Plast. Reconstr. Surg. 113:1634-1644, 2004; Spear and Seruya, Plast. Reconstr. Surg. 125:1074-1084, 2010; Bennett, et al., J. Plast. Reconstr. Aesthet. Surg. 64:1270-1277, 2011). This treatment regimen can prove successful for managing mild infections; however, it has a success rate of approximately 25-30% when it is utilized to treat more severe infections.

A recent report details the addition of lyophilized collagen matrix impregnated with gentamicin upon implant salvage (Lapid, J. Plast. Reconstr. Aesthet. Surg. 64:e313-316, 2011), with subsequent absorption of the collagen carrier. However, collagen is a major component of scar tissue, and the collagen matrix could act as a scaffold for dense scar formation, which would lead to the development of a hard, painful reconstructed breast. Furthermore, once the antibiotic has been offloaded the matrix could act as a potential media for bacterial growth.

Failure of the antibiotic therapy-implant exchange protocol requires removal of the implant for 6-12 months. This often produces contraction (loss of domain) of the reconstructed breast requiring that the rather lengthy and painful tissue expansion process be repeated before a new permanent implant is inserted. Removal of the implant from the augmented breast can produce contracture and soft tissue distortion, impairing the ability to achieve a cosmetically acceptable re-augmentation after completion of the waiting period.

Therefore improved devices and methods to treat periprosthetic breast implant infection would represent a significant advance in the art.

BRIEF SUMMARY OF THE INVENTION

The present disclosure provides improved devices and methods to treat periprosthetic breast implant infections. In addition to improved patient outcome, both physically and psychologically, the benefits of the presently described devices and methods include reduced costs for patients and insurance companies alike.

The present disclosure first provides a breast implant spacer comprising a cement and an antibiotic, antifungal, bacteriostatic or bacteriocidal agent, or any combination thereof. As the breast implant spacer is designed to be inserted in place of the original breast implant, it is designed to substantially resemble the original breast implant. In other words, the breast implant spacer is designed to have a comparable volume and/or a comparable shape to the original breast implant.

The breast implant spacer can comprise a plurality of segments. In an exemplary embodiment, the segments are connected by at least a first pivot pin. The at least a first pivot pin can comprise a number of different materials, including, but not limited to, a polymer, an acrylic cement (which can be loaded with an antibiotic), a metal, or a combination thereof. Polymers suitable for use in manufacture of the at least a first pivot pin include, but are not limited to, ultra-high molecular weight polyethylene, high density polyethylene, acetal homopolymer, polyetheretherketone, acetal polyoxymethylene copolymer, acrylonitrile butadiene styrene, fluorinated ethylene propylene, polytetrafluoroethylene linked to mica, polytetrafluoroethylene, ethylene tetrafluoroethylene, polyphenylene sulfide, polyphenylsulfone, polyethyleneimine, polysulfone, polyethersulfone, polycarbonate, polyphenylene oxide), or a combination thereof. Metals suitable for use in manufacturing the pivot pin include, but are not limited to, stainless steel, titanium, cobalt chromium, or a combination thereof. The segments can also be connected by a first pivot pin and a second pivot pin, which can be made from the same material or different materials. The breast implant spacer can also comprise a suture hole. When the breast implant spacer comprises a plurality of segments, at least two of the plurality of segments can comprise a suture hole.

The segments can also be connected by a wire, which can comprise, for example, stainless steel, DFT®, titanium or a titanium alloy, tantalum, a copper-manganese, copper-nickel, nickel-chromium or quaternary resistance alloy, a mechanical alloy, an austenitic nickel-chromium based superalloy, a HASTELLOY® corrosion-resistant superalloy, or a shape-memory alloy, including, but not limited to, a copper-zinc-aluminum-nickel, copper-aluminum-nickel, or nickel-titanium shape-memory alloy. The segments can also be connected by a spring, which can comprise, for example, stainless steel, DFT®, titanium or a titanium alloy, tantalum, a copper-manganese, copper-nickel, nickel-chromium or quaternary resistance alloy, a mechanical alloy, an austenitic nickel-chromium based superalloy, a HASTELLOY® corrosion-resistant superalloy, or a shape-memory alloy, including, but not limited to, a copper-zinc-aluminum-nickel, copper-aluminum-nickel, or nickel-titanium shape-memory alloy.

In certain embodiments, the breast implant spacer further comprises a template. The template can comprise a biocompatible polymer and/or a metal. Biocompatible polymers suitable for use in preparing the template include, but are not limited to, ultra-high molecular weight polyethylene, high density polyethylene, acetal homopolymer, polyetheretherketone, acetal polyoxymethylene copolymer, acrylonitrile butadiene styrene, fluorinated ethylene propylene, polytetrafluoroethylene linked to mica, polytetrafluoroethylene, ethylene tetrafluoroethylene, polyphenylene sulfide, polyphenylsulfone, polyethyleneimine, polysulfone, polyethersulfone, polycarbonate, poly(p-phenylene oxide), or a combination thereof. Metals suitable for use in the preparation of the template include, but are not limited to, stainless steel, titanium, cobalt chromium, or a combination thereof.

The breast implant spacer can be created from a mold, which can comprise, for example, polyetheretherketone, a medical grade plastic or silicone, ultra-high molecular weight polyethylene, high density polyethylene, acetal homopolymer, acetal polyoxymethylene copolymer, or a combination thereof. The breast implant spacer can also be created from an injectable mold, which can comprise, for example, a medical grade plastic or silicone.

The breast implant spacer can comprise a poly-methyl-methacrylate cement, a methyl-methacrylate-styrene copolymer cement, or a methyl-methacrylate-methyl acrylate cement. In general, the antibiotic, antifungal, bacteriostatic or bacteriocidal agents used in the breast implant spacer do not degrade due to the heat generated upon the cement setting. Suitable antibiotic, antifungal, bacteriostatic or bacteriocidal agents for use in the presently described breast implant spacers include, but are not limited to, vancomycin, tobramycin, voriconazole, gentamicin, erythromycin, oxacillin, cloxacillin, methicillin, lincomycin, ampicillin, colistin, clindamycin, a cephalosporin, amphotericin B, fluconazole, copper-nitride, metallic silver, or any combination thereof.

The present disclosure also provides a breast implant spacer comprising plurality of segments, each of said segments comprising a poly-methyl-methacrylate cement and vancomycin, tobramycin, voriconazole, or any combination thereof, said plurality of segments connected by a first pivot pin and a second pivot pin, wherein the spacer is designed to approximate a volume and a shape of a breast implant.

The present disclosure further provides a breast implant spacer comprising plurality of segments, each of said segments comprising a poly-methyl-methacrylate cement and vancomycin, tobramycin, voriconazole, or any combination thereof, said plurality of segments connected by a spring, wherein the spacer is designed to approximate a volume and a shape of a breast implant.

The present disclosure additionally provides a mold for forming a breast implant spacer, comprising a base defining a concave indentation and a convex plunger comprising a plurality of projections, the mold approximating or substantially comparable to the volume and/or the shape of a breast implant. Furthermore, the present disclosure provides an injectable mold for forming a breast implant spacer, comprising an outer shell comprising a convex first portion and a flat second portion, having a plurality of fill ports, a plurality of air efflux ports, and a plurality of septal anchors, and an internal bladder having a liquid fill port, said plurality of septal anchors stabilizing said internal bladder within said convex first portion and said flat second portion, the injectable mold approximating or substantially comparable to the volume and the shape of a breast implant.

The present disclosure also provides a method of making an antibiotic breast implant spacer, comprising introducing a mixture of a cement and an antibiotic into a mold that approximates or is comparable to the volume and the shape of a breast implant, allowing the mixture to set to form the antibiotic breast implant spacer, and removing the antibiotic breast implant spacer from the mold. The mold can comprise, for example, polyetheretherketone, a medical grade plastic or silicone, ultra-high molecular weight polyethylene, high density polyethylene, acetal homopolymer, acetal polyoxymethylene copolymer, or a combination thereof. The mold can also be an injectable mold, which can comprise, for example, a medical grade plastic or silicone, or a combination thereof. The antibiotic breast implant spacer can also be cut into segments.

The present disclosure further provides a method of treating a breast implant infection in a patient in need of such treatment, comprising replacing the breast implant with a breast implant spacer comprising a cement and an antibiotic, wherein the spacer is designed to approximate or be comparable to a volume and a shape of the breast implant.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" may mean a singular object or element, or it may mean a plurality, or one or more of such objects or elements.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The present disclosure is directed to improved devices and methods to treat periprosthetic breast implant infections. The present disclosure specifically addresses the formulation, preparation and use of antibiotic spacers that approximate the volume and shape of the existing breast implant. In general the antibiotic spacers comprise a cement, such as a bone cement, and an antibiotic, antifungal, bacteriostatic or bacteriocidal agent, or any combination thereof. In certain embodiments the antibiotic spacers comprise a plurality of connected segments. In further embodiments the antibiotic spacers could be formed by coating at least a portion of metallic or plastic template with a cement and an antibiotic, antifungal, bacteriostatic or bacteriocidal agent.

Figure 1:
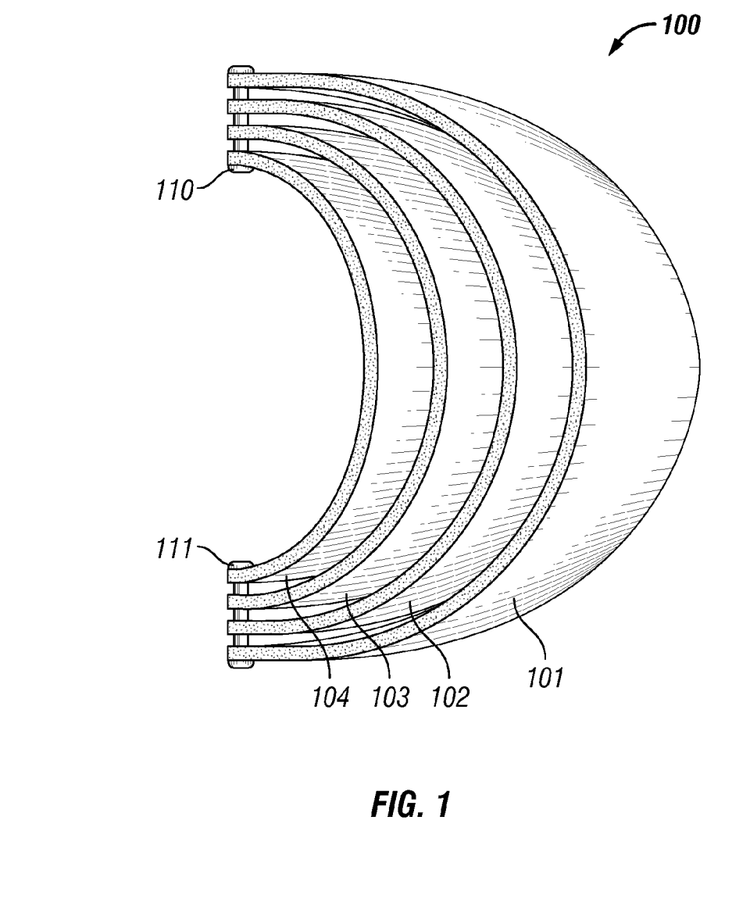
FIG. 1. A side view of an embodiment of a four segment articulated antibiotic spacer of the present disclosure.

FIG. 1 shows a side view of one embodiment of an antibiotic spacer 100 of the present disclosure. In this embodiment antibiotic spacer 100 is comprised of four segments, 101, 102, 103 and 104, which are connected by pivot pins 110 and 111 such that the segments 101, 102, 103 and 104 can rotate on the pivot pins 110 and 111 to form a generally circular shape (see FIG. 2). Each of segments 101, 102, 103 and 104 are comprised of a cement, such as a bone cement, that is impregnated with one or more antibiotics. The skilled artisan will appreciate that in such embodiments the number of segments is not important, and can vary from 2 to 8 or more (not shown) depending upon the particular requirements of the spacer. In addition, the segments can be connected with a single pivot pin (not shown). The dimensions of the antibiotic spacer can vary, depending upon the particular application, but in general the diameter can range between about 9 cm and about 16 cm, the height (or projection) can range between about 3 cm and about 8 cm, and the thickness can range between about 5 mm and about 1 cm.

A number of different materials can be used to fabricate pivot pins 110 and 111, including, but not limited to, a polymer such as ultra-high molecular weight polyethylene, high density polyethylene, acetal homopolymer (DELRIN®), polyetheretherketone (PEEK), acetal polyoxymethylene (POM) copolymer (CELCON®, ULTRAFORM®, ACETRON® GP), acrylonitrile butadiene styrene (ABS), fluorinated ethylene propylene (FEP), polytetrafluoroethylene (PTFE) linked to mica (FLUOROSINT®), PTFE (TEFLON®), ethylene tetrafluoroethylene (ETFE; TEFZEL®), polyphenylene sulfide (PPS; FORTRON®), polyphenylsulfone (PPSU; RADEL®), polyethyleneimine (PEI), polysulfone (PSU; ULTRASON® S), polyethersulfone (PES; ULTRASON® E), polycarbonate (PC), poly(p-phenylene oxide) (PPO), acrylic cement (which is certain instances can be loaded with an antibiotic), or metal, such as stainless steel, titanium or cobalt chromium, or any combination thereof.

A number of different cements or combination of cements can be used to fabricate the antibiotic spacer. In general, such cements or combination of cements are solid enough to maintain the shape of the breast implant throughout most or all of the procedure, while at the same time porous enough to allow a sufficient or therapeutically effective amount of antibiotic (or combination of antibiotics) to diffuse from the cement to treat or cure the infection. For example cements that can be used include, but are not limited to, bone cements, such as a poly-methyl-methacrylate (PMMA) cement, including those produced under the trade names Generation 4™, CMW1, CMW2, CMW3, Zimmer Dough Type, Zimmer LVC, SMARTSET® MV, SMARTSET® GMV, or SMARTSET® GHV, a MMA-styrene copolymer cement, including those produced under the trade names Stryker® Simplex™ P or Zimmer OSTEOBOND®, or an MMA-methyl acrylate copolymer cement, including those produced under trade name Cobalt™ G-HV, Cobalt™ HV, or PALACOS® R.

A number of different antibiotic, antifungal, bacteriostatic or bacteriocidal agents, or any combination thereof, can be used in the antibiotic spacer. In general, such antibiotic, antifungal, bacteriostatic or bacteriocidal agents, or combination thereof, are stable enough to withstand the heat generated during the curing of the cement (or combination of cements) used to fabricate the antibiotic spacer. The choice of antibiotic, antifungal, bacteriostatic or bacteriocidal agent for the spacer may depend upon the source of an actual infection or potential infection, and include, but is not limited to, vancomycin, tobramycin, voriconazole gentamicin, erythromycin, oxacillin, cloxacillin, methicillin, lincomycin, ampicillin, colistin, clindamycin, a cephalosporin, amphotericin B, fluconazole, copper-nitride, metallic silver, or any combination thereof.

Figure 2:
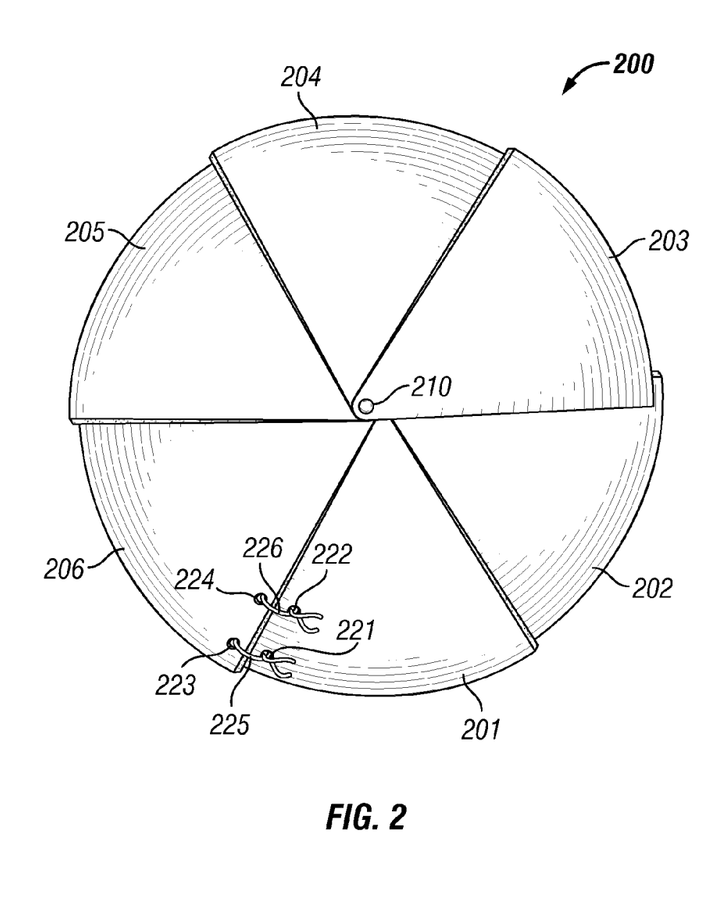
FIG. 2. A top view of an embodiment of a six segment articulated antibiotic spacer of the present disclosure.

FIG. 2 shows a top view of another embodiment of an antibiotic spacer 200 of the present disclosure. In this embodiment antibiotic spacer 200 is comprised of six segments, 201, 202, 203, 204, 205 and 206, which are connected by pivot pin 210 such that the segments 201, 202, 203, 204, 205 and 206 can rotate on the pivot pin 210 to form a generally circular shape. Also shown are suture holes 221, 222, 223 and 224, which are connected by sutures 225 and 226. The skilled artisan will appreciate that in such embodiments the number of suture holes is not important, and can vary from 1 to 4 or more (not shown) depending upon the particular requirements of the spacer. In addition, the suture holes can be connected with wire or any other suitable material (not shown).

Figure 3:
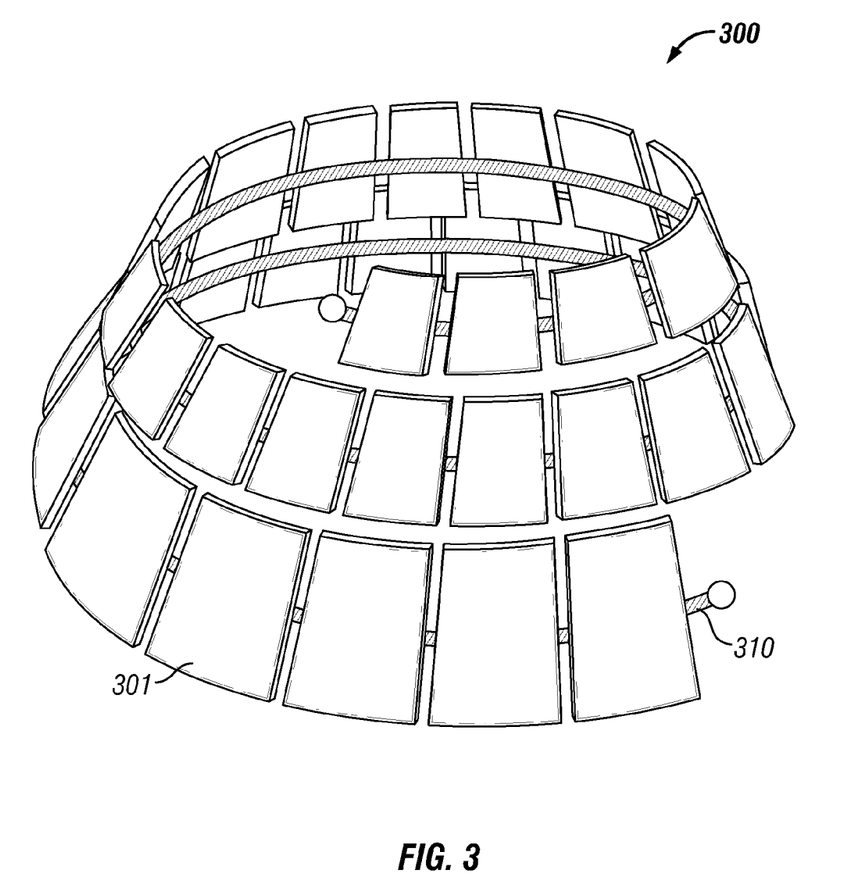
FIG. 3. A perspective view of an embodiment of a segmented, spring loaded antibiotic spacer of the present disclosure.

FIG. 3 shows a perspective view of another embodiment of an antibiotic spacer 300 of the present disclosure. In this embodiment antibiotic spacer 300 is comprised of a plurality of segments 301 that are connected by a spring 310. The skilled artisan will appreciate that in such embodiments the size and number of segments 301, the total length of the spring 310, as well as the distance between the segments 301 on the spring 310 can vary as described herein above depending upon the particular needs of the patient. In certain embodiments (not shown) the segments 301 can be connected by one or more wires, for example wires comprising stainless steel, DFT®, titanium or a titanium alloy, tantalum, a copper-manganese, copper-nickel, nickel-chromium or quaternary resistance alloy (i.e., BALCO® 120, INCOLOY® alloy 800), a mechanical alloy (i.e., MONEL® 400), an austenitic nickel-chromium based superalloy (i.e., ICONEL®) or a HASTEL-LOY® corrosion-resistant superalloy, or wires fabricated from a shape-memory alloy. The most common types of shape-memory alloys are the copper-zinc-aluminum-nickel, copper-aluminum-nickel, and nickel-titanium (NiTi) alloys, but shape-memory alloys can also be created by alloying zinc, copper, gold and iron.

Figure 4:
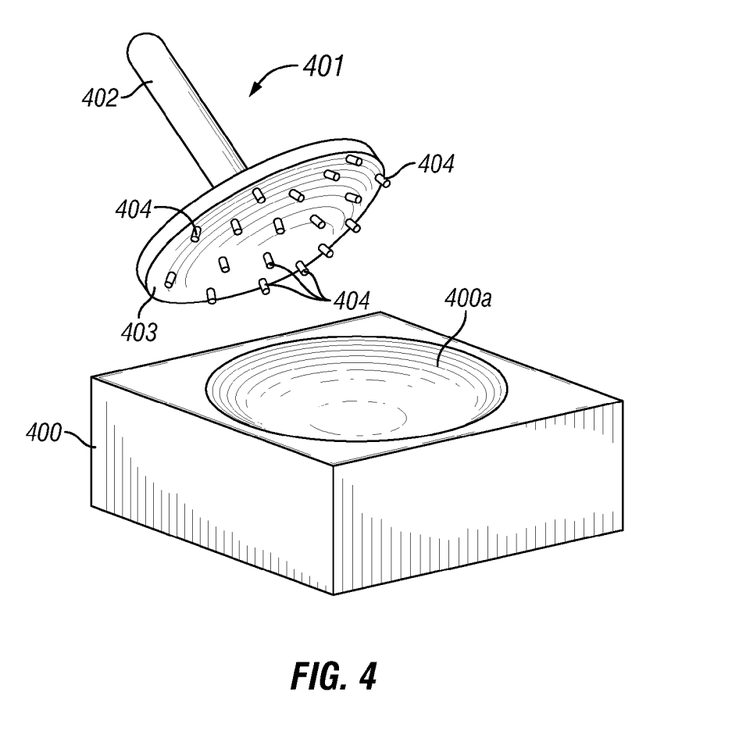
FIG. 4. A perspective view of an embodiment of a mold base and mold insert used to form an antibiotic spacer of the present disclosure.

FIG. 4 shows a perspective view of an embodiment of a mold base 400 and mold plunger 401 used to form an embodiment of an antibiotic spacer of the present disclosure. In this embodiment the mold base 400 has a cut-out or indentation having a concave surface 400a that approximates the shape of the breast implant (not shown) from the patient, and the mold plunger 401 comprises a handle 402, a head 403, and a plurality of projections 404 connected to the head 404, which can vary in length depending upon the desired thickness of the antibiotic spacer. To form an antibiotic spacer using the mold shown in FIG. 4, the desired amount of a mixture of cement and antibiotic(s) (not shown) is poured onto the concave surface 400a of the mold base 400 to reach the desired thickness of the antibiotic spacer, and the mold plunger 401 is inserted into the cement/antibiotic(s) mixture. Once the cement/antibiotic(s) mixture hardens, cures or sets to form the antibiotic spacer, the plunger 401 is removed from the antibiotic spacer, and the antibiotic spacer is removed from the concave surface 400a of the mold base 400. In certain embodiments the antibiotic spacer thus formed can be cut into a plurality of segments prior to use.

Any suitable material can be used to form the mold base 400 and plunger 401, including, but not limited to, medical grade plastic or silicone, such as DOW CORNING® SILASTIC® Q7-4780 or any other 80 durometer silicone, ultra-high molecular weight polyethylene, high density polyethylene, PEEK, acetal homopolymer (DELRIN®), or acetal polyoxymethylene (POM) copolymer (CELCON®, ULTRAFORM®, ACETRON® GP). In general the material used to form the mold base 400 and plunger 401 should be flexible to ease removal of the hardened or cured antibiotic spacer, but solid enough to maintain its shape when the cement/antibiotic mixture is added to the mold base 400, and the plunger 401 is inserted into the cement/antibiotic mixture. In addition the material should not react adversely with the cement/antibiotic mixture, or cause breakdown of the cement or the antibiotic in the mixture.

Figure 5:
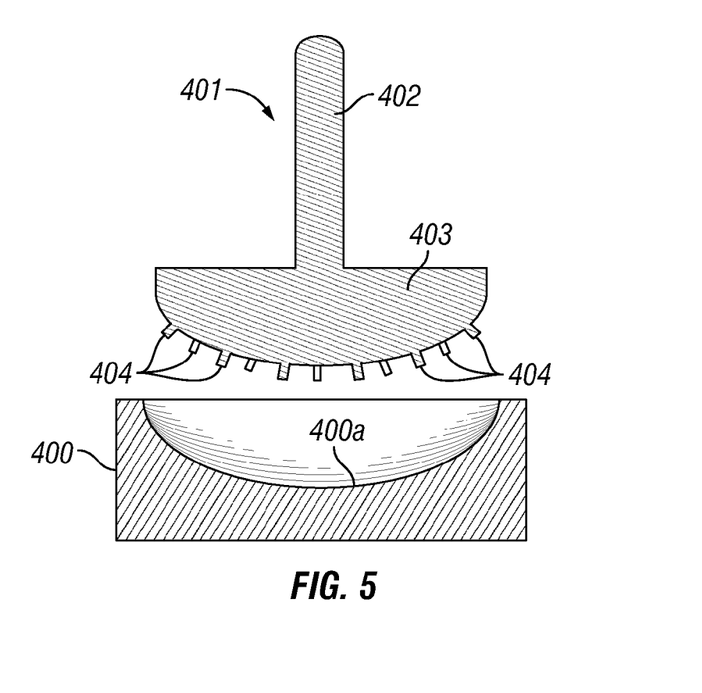
FIG. 5. A side view of an embodiment of a mold base and a mold spacer used to form an antibiotic spacer of the present disclosure.

FIG. 5 shows a side view of the embodiment of a mold base 400 and a mold plunger 401 shown in FIG. 4, which can be used to form an embodiment of an antibiotic spacer of the present disclosure. Once again, the mold base 400 has a concave surface 400a that approximates the shape of the breast implant (not shown) from the patient, and the mold plunger 401 comprises a handle 402, a head 403, and a plurality of projections 404 connected to the head 404, which can vary in length depending upon the desired thickness of the antibiotic spacer.

Figure 6:
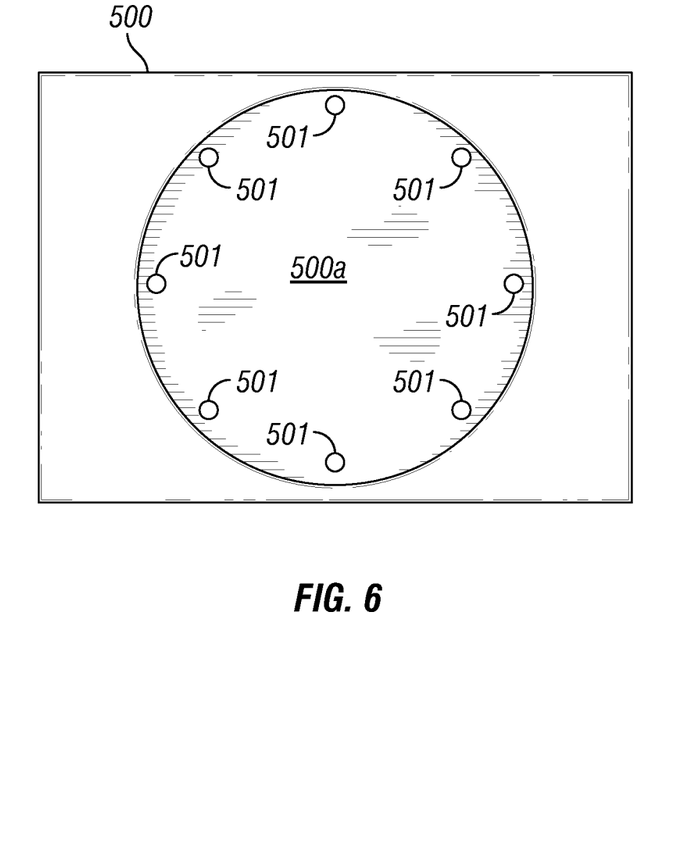
FIG. 6. A top view of an embodiment of a mold base used to form an antibiotic spacer of the present disclosure.

FIG. 6 shows a top view of an embodiment of a mold base 500 used to form an embodiment of an antibiotic spacer of the present disclosure. The mold base 500 defines a cut-out portion 500a, which in this embodiment is generally circular in shape. In other embodiments (not shown) the cut-out portion can have a generally triangular, square, or rectangular shape, or any other shape desired to construct an antibiotic spacer of the present disclosure. The mold base 500 also comprises a plurality (in this embodiment seven) pegs or projections 501, which are used to form holes for sutures or wires. The skilled artisan will appreciate that in such embodiments the number of pegs or projections 501 is not important, and can vary from 0, 1, 2, 3, 4, 5 or 6 or more (not shown) depending upon the particular requirements of the spacer. To form an antibiotic spacer using the mold shown in FIG. 6, the desired amount of a mixture of cement and antibiotic(s) (not shown) is poured into the cut-out portion 500a of the mold base 500 to reach the desired thickness of the antibiotic spacer. Once the cement/antibiotic(s) mixture hardens, cures or sets to form the antibiotic spacer, the antibiotic spacer is removed from the cut-out portion 500a of the mold base 500. In certain embodiments the antibiotic spacer thus formed can be cut into a plurality of segments prior to use.

Figure 7:
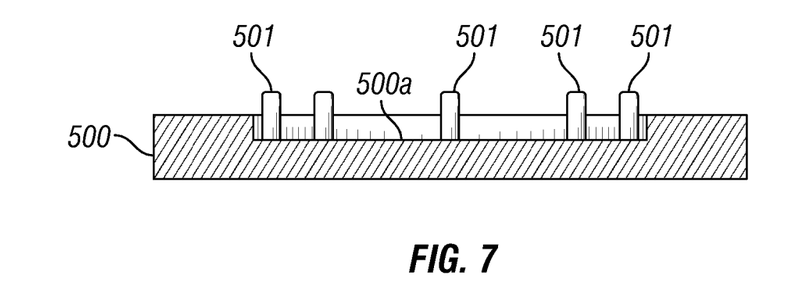
FIG. 7. A side view of an embodiment of a mold base used to form an antibiotic spacer of the present disclosure.

FIG. 7 shows a side view of an embodiment of a mold base used to form an antibiotic spacer of the present disclosure. Once again, the mold base 500 has a cut-out portion 500a and a plurality of pegs or projections 501. Although the bottom of the cut-out portion 500a is flat in this embodiment, the bottom can be concave in further embodiments of the disclosure (not shown).

Figure 8:
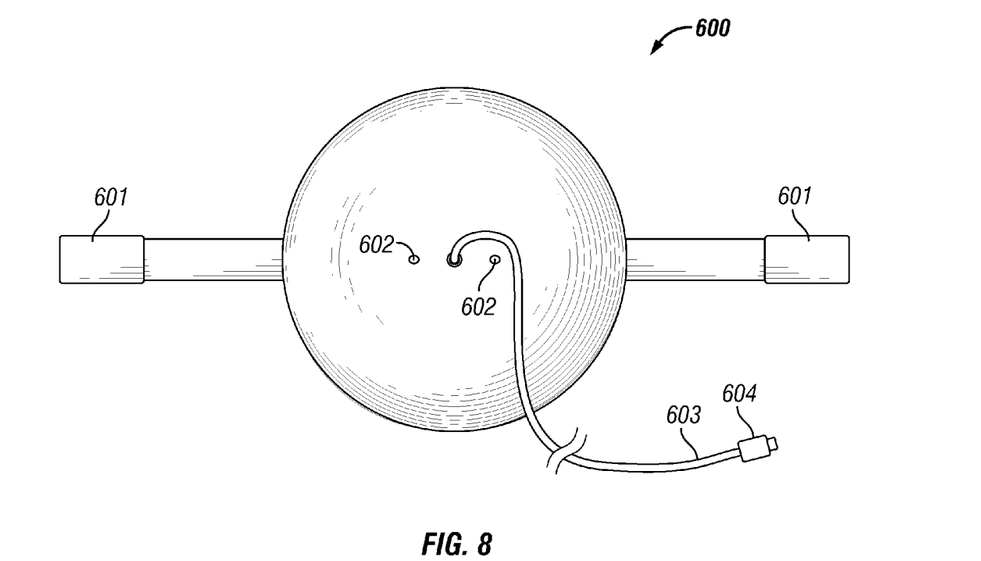
FIG. 8. A top view of an embodiment of an injectable mold used to form an antibiotic spacer of the present disclosure.

FIG. 8 shows a top view of an embodiment of an injectable mold 600 used to form an embodiment of an antibiotic spacer of the present disclosure. Mold 600 comprises two threaded injection/fill ports 601 two air efflux ports 602 and a fill port 603 with a fitting 604 (in this embodiment a luer-lock fitting) that is connected to the internal bladder (not shown in FIG. 8; see FIG. 9). This embodiment of the injectable mold 600 is generally circular in shape, although in alternative embodiments (not shown) the injectable mold can generally triangular, square or rectangular in shape, or any other desired shape. Any suitable material can be used to form the injectable mold 600, including, but not limited to, medical grade plastic or silicone, such as DOW CORNING® SILASTIC® Q7-4780 or any other 80 durometer silicone.

Figure 9:
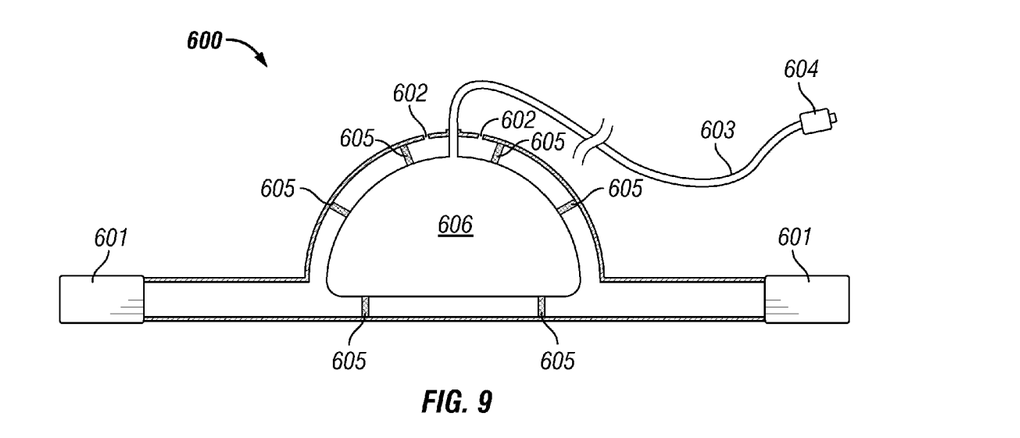
FIG. 9. A side view of an embodiment of an injectable mold used to form an antibiotic spacer of the present disclosure.

FIG. 9 shows a side view of the embodiment of the injectable mold shown in FIG. 8, which can be used to form an embodiment of an antibiotic spacer of the present disclosure. Once again mold 600 comprises two threaded injection/fill ports 601 two air efflux ports 602 and a fill port 603 with a fitting 604 (in this embodiment a luer-lock fitting) that is connected to the internal bladder 606. Internal bladder can be filled with any suitable material to define the shape of the antibiotic spacer, including, but not limited to, water, saline, silicone, air or nitrogen. Also shown in FIG. 9 are septations 605 that prevent movement of the internal bladder 606 with respect to the mold 600. To form an antibiotic spacer using the mold 600, the desired amount of a mixture of cement and antibiotic(s) (not shown) is poured or pumped into one of the injection/fill ports 601, and fluid or gas is added to the internal bladder 606 to reach the desired thickness of the antibiotic spacer. Once the cement/antibiotic(s) mixture hardens, cures or sets to form the antibiotic spacer, the antibiotic spacer is removed from the mold 600 by sharply incising the silicone outer layer, leaving the inner bladder intact. In certain embodiments the antibiotic spacer thus formed can be cut into a plurality of segments prior to use.

The following example is included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims.

EXAMPLE 1

Antibiotic impregnated spacers provide a new and effective method for treating periprosthetic breast implant infections. The patient is returned to the operating room for removal of the infected implant and debridement. An antibiotic impregnated spacer fashioned to replicate the shape and volume of the removed breast implant is inserted. The spacer is composed of polymethymethacrylate and contains all or combinations of vancomycin, tobramycin and voriconazole. After the implant is inserted the access incision is closed. Over a period of 4 weeks the implant will release its antibiotic load achieving local concentrations up to and exceeding 100 times the MIC (mean inhibitory concentration). The supraphysiologic antibiotic concentration is highly bactericidal yet produces minimal systemic absorption avoiding nephrotoxicity and ototoxicity. In addition to managing local infection the spacer maintains the shape and volume of the breast avoiding the need for repeat expansion in the reconstructed breast and reducing the potential for disfiguring contracture in cases of cosmetic augmentation. The spacer is used in conjunction with systemic antibiotic therapy. After a 6-12 week period the patient is returned to the operating room for removal of the spacer and insertion of a permanent breast implant.

A female who underwent bilateral simple mastectomy followed by uncomplicated expander-implant breast reconstruction was chosen to test the antibiotic impregnated spacer. Fourteen months after the initial surgery the patient underwent bilateral nipple reconstruction complicated by development of swelling, pain and erythema of the right breast. She was returned to the operating room where irrigation and debridement was performed. Cultures were obtained and the original implant was cleansed and replaced. Operative cultures demonstrated Methocillin Resistant *Staphlococcus Auerus* (MRSA) and she received a course of culture specific intravenous antibiotics. Despite this intervention the infection recurred and she was returned to the operating room for removal of the implant, debridement and insertion of an antibiotic spacer containing vancomycin and tobramycin. Repeat cultures again demonstrated MRSA. She received a short course of intravenous antibiotics followed by a 4 week course of oral antibiotics. During the $7^{th}$ postoperative week the patient was returned to surgery for removal of the spacer and insertion of a permanent breast implant. The patient has been followed for 18 months and no sign of recurrent infection or capsular contracture has developed. The overall aesthetics of the reconstruction are good and the treatment at this juncture can be deemed a success.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A breast implant spacer comprising a cement and an antibiotic, antifungal, bacteriostatic or bacteriocidal agent, or a combination thereof, wherein the spacer comprises a plurality of segments that are connected by at least a first pivot pin, a wire, or a spring.

2. The breast implant spacer of claim 1, wherein the spacer is designed to substantially resemble a breast implant.

3. The breast implant spacer of claim 1, wherein the spacer is designed to have a comparable volume or a comparable shape of a breast implant.

4. The breast implant spacer of claim 1, wherein the plurality of segments are connected by at least a first pivot pin.

5. The breast implant spacer of claim 4, wherein the at least a first pivot pin comprises a polymer, an acrylic cement, a metal, or a combination thereof.

6. The breast implant spacer of claim 5, wherein the at least a first pivot pin comprises a polymer.

7. The breast implant spacer of claim 6, wherein the at least a first pivot pin comprises ultra-high molecular weight polyethylene, high density polyethylene, acetal homopolymer, polyetheretherketone, acetal polyoxymethylene copolymer, acrylonitrile butadiene styrene, fluorinated ethylene propylene, polytetrafluoroethylene linked to mica, polytetrafluoroethylene, ethylene tetrafluoroethylene, polyphenylene sulfide, polyphenylsulfone, polyethyleneimine, polysulfone, polyethersulfone, polycarbonate, poly(p-phenylene oxide), or a combination thereof.

8. The breast implant spacer of claim 5, wherein the at least a first pivot pin comprises a metal.

9. The breast implant spacer of claim 8, wherein the at least a first pivot pin comprises stainless steel, titanium, cobalt chromium, or a combination thereof.

10. The breast implant spacer of claim 5, wherein the at least a first pivot pin comprises an acrylic cement.

11. The breast implant spacer of claim 10, wherein the acrylic cement is loaded with an antibiotic.

12. The breast implant spacer of claim 4, wherein the plurality of segments are connected by a first pivot pin and a second pivot pin.

13. The breast implant spacer of claim 1, wherein the plurality of segments are connected by a wire.

14. The breast implant spacer of claim 13, wherein the wire comprises stainless steel, DFT®, titanium or a titanium alloy, tantalum, a copper-manganese, copper-nickel, nickel-chromium or quaternary resistance alloy, a mechanical alloy, an austenitic nickel-chromium based superalloy, a HASTELLOY® corrosion-resistant superalloy, or a shape-memory alloy.

15. The breast implant spacer of claim 14, wherein the wire comprises a shape-memory alloy.

16. The breast implant spacer of claim 15, wherein the shape-memory alloy is a copper-zinc-aluminum-nickel, copper-aluminum-nickel, or nickel-titanium shape-memory alloy.

17. The breast implant spacer of claim 1, wherein the plurality of segments are connected by a spring.

18. The breast implant spacer of claim 17, wherein the spring comprises stainless steel, DFT®, titanium or a titanium alloy, tantalum, a copper-manganese, copper-nickel, nickel-chromium or quaternary resistance alloy, a mechanical alloy, an austenitic nickel-chromium based superalloy, a HASTELLOY® corrosion-resistant superalloy, or a shape-memory alloy.

19. The breast implant spacer of claim 18, wherein the spring comprises stainless steel.

20. The breast implant spacer of claim 1, further comprising a template.

21. The breast implant spacer of claim 20, wherein the template comprises a biocompatible polymer or a metal.

22. The breast implant spacer of claim 21, wherein the template comprises a biocompatible polymer.

23. The breast implant spacer of claim 22, wherein the template comprises ultra-high molecular weight polyethylene, high density polyethylene, acetal homopolymer, polyetheretherketone, acetal polyoxymethylene copolymer, acrylonitrile butadiene styrene, fluorinated ethylene propylene, polytetrafluoroethylene linked to mica, polytetrafluoroethylene, ethylene tetrafluoroethylene, polyphenylene sulfide, polyphenylsulfone, polyethyleneimine, polysulfone, polyethersulfone, polycarbonate, poly(p-phenylene oxide), or a combination thereof.

24. The breast implant spacer of claim 21, wherein the template comprises a metal.

25. The breast implant spacer of claim 24, wherein the template comprises stainless steel, titanium, cobalt chromium, or a combination thereof.

26. The breast implant spacer of claim 1, wherein the breast implant spacer comprises a suture hole.

27. The breast implant spacer of claim 1, wherein at least two of the plurality of segments comprise a suture hole.

28. The breast implant spacer of claim 1, wherein the breast implant spacer is created from a mold.

29. The breast implant spacer of claim 28, wherein the mold comprises a medical grade plastic or silicone, ultra-high molecular weight polyethylene, high density polyethylene, acetal homopolymer, acetal polyoxymethylene copolymer, or a combination thereof.

30. The breast implant spacer of claim 28, wherein the breast implant spacer is created from an injectable mold.

31. The breast implant spacer of claim 30, wherein the injectable mold comprises a medical grade plastic or silicone.

32. The breast implant spacer of claim 1, wherein the cement is a poly-methyl-methacrylate cement, a methyl-methacrylate-styrene copolymer cement, or a methyl-methacrylate-methyl acrylate cement.

33. The breast implant spacer of claim 32, wherein the cement is a poly-methyl-methacrylate cement.

34. The breast implant spacer of claim 1, wherein said antibiotic, antifungal, bacteriostatic or bacteriocidal agent does not degrade upon the cement setting.

35. The breast implant spacer of claim 34, wherein the antibiotic, antifungal, bacteriostatic or bacteriocidal agent is vancomycin, tobramycin, voriconazole, gentamicin, erythromycin, oxacillin, cloxacillin, methicillin, lincomycin, ampicillin, colistin, clindamycin, a cephalosporin, amphotericin B, fluconazole, copper-nitride, metallic silver, or any combination thereof.

36. The breast implant spacer of claim 35, wherein the antibiotic, antifungal, bacteriostatic or bacteriocidal agent is vancomycin, tobramycin, voriconazole, or any combination thereof.

37. A breast implant spacer comprising plurality of segments, each of said segments comprising a poly-methyl-methacrylate cement and vancomycin, tobramycin, voriconazole, or any combination thereof, said plurality of segments connected by a first pivot pin and a second pivot pin.

38. A breast implant spacer comprising plurality of segments, each of said segments comprising a poly-methyl-methacrylate cement and vancomycin, tobramycin, voriconazole, or any combination thereof, said plurality of segments connected by a spring.

* * * * *

UNITED STATES PATENT AND TRADEMARK OFFICE
CERTIFICATE OF CORRECTION

Page 1 of 4

PATENT NO. : 8,808,372 B2
APPLICATION NO. : 13/458647
DATED : August 19, 2014
INVENTOR(S) : Michael Klebuc et al.

It is certified that error appears in the above-identified patent and that said Letters Patent is hereby corrected as shown below:

Delete the title page and substitute the attached title page therefor.

In the Claims

Column 12, Line 37, after Claim 38 please insert the following claims:

--39. A method of treating a breast implant infection in a patient in need of such treatment, comprising replacing the breast implant with a breast implant spacer comprising a cement and an antibiotic, antifungal, bacteriostatic or bacteriocidal agent, or combination thereof, wherein the spacer comprises a plurality of segments that are connected by at least a first pivot pin, a wire, or a spring.
40. The method of claim 39, wherein the spacer is designed to substantially resemble a breast implant.
41. The method of claim 39, wherein the spacer is designed to have a comparable volume or a comparable shape of a breast implant.
42. The method of claim 39, wherein the plurality of segments are connected by at least a first pivot pin.
43. The method of claim 42, wherein the at least a first pivot pin comprises a polymer, an acrylic cement, a metal or a combination thereof.
44. The method of claim 43, wherein the at least a first pivot pin comprises a polymer.
45. The method of claim 44, wherein the at least a first pivot pin comprises ultra high molecular weight polyethylene, high density polyethylene, acetal homopolymer, polyetheretherketone, acetal polyoxymethylene copolymer, acrylonitrile butadiene styrene, fluorinated ethylene propylene, polytetrafluoroethylene linked to mica, polytetrafluoroethylene, ethylene tetrafluoroethylene, polyphenylene sulfide, polyphenylsulfone, polyethyleneimine, polysulfone, polyethersulfone, polycarbonate, poly(p phenylene oxide), or a combination thereof.
46. The method of claim 43, wherein the at least a first pivot pin comprises a metal.
47. The method of claim 46, wherein the at least a first pivot pin comprises stainless steel, titanium, cobalt chromium, or a combination thereof.
48. The method of claim 43, wherein the at least a first pivot pin comprises an acrylic cement.

Signed and Sealed this
Sixteenth Day of December, 2014

Michelle K. Lee
*Deputy Director of the United States Patent and Trademark Office*

49. The method of claim 48, wherein the acrylic cement is loaded with an antibiotic.
50. The method of claim 42, wherein the plurality of segments are connected by a first pivot pin and a second pivot pin.
51. The method of claim 39, wherein the plurality of segments are connected by a wire.
52. The method of claim 51, wherein the wire comprises stainless steel, DFT®, titanium or a titanium alloy, tantalum, a copper-manganese, copper-nickel, nickel-chromium or quaternary resistance alloy, a mechanical alloy, an austenitic nickel-chromium based superalloy, a HASTELLOY® corrosion-resistant superalloy, or a shape-memory alloy.
53. The method of claim 52, wherein the wire comprises a shape-memory alloy.
54. The method of claim 53, wherein the shape-memory alloy is a copper-zinc-aluminum-nickel, copper-aluminum-nickel, or nickel-titanium shape-memory alloy.
55. The method of claim 39, wherein the plurality of segments are connected by a spring.
56. The method of claim 55, wherein the spring comprises stainless steel, DFT®, titanium or a titanium alloy, tantalum, a copper-manganese, copper-nickel, nickel-chromium or quaternary resistance alloy, a mechanical alloy, an austenitic nickel-chromium based superalloy, a HASTELLOY® corrosion-resistant superalloy, or a shape-memory alloy.
57. The method of claim 56, wherein the spring comprises stainless steel.
58. The method of claim 39, wherein the breast implant spacer further comprises a template.
59. The method of claim 58, wherein the template comprises a biocompatible polymer or a metal.
60. The method of claim 59, wherein the template comprises a biocompatible polymer.
61. The method of claim 60, wherein the template comprises ultra-high molecular weight polyethylene, high density polyethylene, acetal homopolymer, polyetheretherketone, acetal polyoxymethylene copolymer, acrylonitrile butadiene styrene, fluorinated ethylene propylene, polytetrafluoroethylene linked to mica, polytetrafluoroethylene, ethylene tetrafluoroethylene, polyphenylene sulfide, polyphenylsulfone, polyethyleneimine, polysulfone, polyethersulfone, polycarbonate, poly(p phenylene oxide), or a combination thereof.
62. The method of claim 59, wherein the template comprises a metal.
63. The method of claim 62, wherein the template comprises stainless steel, titanium, cobalt chromium, or a combination thereof.
64. The method of claim 39, wherein the breast implant spacer comprises a suture hole.
65. The method of claim 39, wherein at least two of the plurality of segments comprise a suture hole.
66. The method of claim 39, wherein the breast implant spacer is created from a mold.
67. The method of claim 66, wherein the mold comprises a medical grade plastic or silicone, ultra-high molecular weight polyethylene, high density polyethylene, acetal homopolymer, acetal polyoxymethylene copolymer, or a combination thereof.
68. The method of claim 66, wherein the breast implant spacer is created from an injectable mold.
69. The method of claim 68, wherein the injectable mold comprises a medical grade plastic or silicone.
70. The method of claim 39, wherein the cement is a poly-methyl-methacrylate cement, a methyl-methacrylate styrene copolymer cement, or a methyl-methacrylate-methyl acrylate cement.
71. The method of claim 70, wherein the cement is a poly-methyl-methacrylate cement.
72. The method of claim 39, wherein said antibiotic, antifungal, bacteriostatic or bacteriocidal agent does not degrade upon the cement setting.

73. The method of claim 72, wherein the antibiotic, antifungal, bacteriostatic or bacteriocidal agent is vancomycin tobramycin, voriconazole, gentamicin, erythromycin, oxacillin, cloxacillin, methicillin, lincomycin, ampicillin, colistin clindamycin, a cephalosporin, amphotericin B, fluconazole, copper-nitride, metallic silver, or any combination thereof.

74. The method of claim 73, wherein the antibiotic, antifungal, bacteriostatic or bacteriocidal agent is vancomycin tobramycin, voriconazole, or any combination thereof.--

(12) United States Patent
Klebuc et al.

(10) Patent No.: US 8,808,372 B2
(45) Date of Patent: Aug. 19, 2014

(54) BREAST IMPLANT SPACERS FOR THE TREATMENT OF PERIPROSTHETIC BREAST IMPLANT INFECTIONS

(75) Inventors: Michael Klebuc, Houston, TX (US); Elizabeth Ann Welter, Houston, TX (US)

(73) Assignee: Cold Winter Solutions, L.L.C., Houston, TX (US)

(*) Notice: Subject to any disclaimer, the term of this patent is extended or adjusted under 35 U.S.C. 154(b) by 249 days.

(21) Appl. No.: 13/458,647

(22) Filed: Apr. 27, 2012

(65) Prior Publication Data
US 2013/0289721 A1 Oct. 31, 2013

(51) Int. Cl.
A61F 2/12 (2006.01)

(52) U.S. Cl.
USPC .................................................. 623/8

(58) Field of Classification Search
USPC ............................................... 623/7-8
See application file for complete search history.

(56) References Cited

U.S. PATENT DOCUMENTS

| | | |
|---|---|---|
| 4,298,997 A | 11/1981 | Rybka |
| 4,846,844 A | 7/1989 | DeLeon et al. |
| 4,952,419 A | 8/1990 | DeLeon et al. |
| 5,133,771 A | 7/1992 | Duncan et al. |
| 5,618,286 A | 4/1997 | Brinker |
| 6,155,812 A | 12/2000 | Smith et al. |
| 6,361,731 B1 | 3/2002 | Smith et al. |
| 6,942,475 B2 | 9/2005 | Ensign et al. |
| 7,427,296 B2 | 9/2008 | Evans |
| 7,429,346 B2 | 9/2008 | Ensign et al. |
| 7,637,729 B2 | 12/2009 | Hartman et al. |
| 7,842,095 B2 | 11/2010 | Klein |
| 7,867,426 B2 * | 1/2011 | Zirun et al. |
| 2009/0216323 A1 * | 8/2009 | Ledergerber ............ 623/8 |
| 2010/0168808 A1 | 7/2010 | Citron |
| 2010/0198350 A1 | 8/2010 | Berg et al. |
| 2011/0009960 A1 * | 1/2011 | Altman et al. ............ 623/8 |
| 2011/0082545 A1 | 4/2011 | Freund |
| 2011/0082546 A1 * | 4/2011 | Freund ............ 623/8 |
| 2011/0106248 A1 | 5/2011 | Kokott et al. |
| 2011/0137244 A1 * | 6/2011 | Lee et al. ............ 604/103.02 |
| 2011/0137412 A1 | 6/2011 | Nyte |
| 2011/0153017 A1 | 6/2011 | McClellan |
| 2011/0160854 A1 * | 6/2011 | Berg et al. ............ 623/8 |
| 2011/0262511 A1 | 10/2011 | Love et al. |
| 2012/0052292 A1 * | 3/2012 | Pulapura et al. ............ 428/336 |
| 2012/0221105 A1 * | 8/2012 | Altman et al. ............ 623/8 |
| 2012/0253460 A1 * | 10/2012 | Ledergerber ............ 623/8 |
| 2014/0039617 A1 * | 2/2014 | Maxwell ............ 623/8 |

FOREIGN PATENT DOCUMENTS

GB 2040688 A 9/1980

OTHER PUBLICATIONS

Bennett, et al., "Management of exposed, infected implant-based breast reconstruction and strategies for salvage," J. Plast. Reconstr. Aesthet. Surg. 64:1270-1277, 2011.

Courtiss, et al., "The fate of breast implants with infections around them," Plast. Reconstr. Surg. 63:812-816, 1979.

Cui, et al., "Antibiotic-impregnated cement spacers for the treatment of infection associated with total hip or knee arthroplasty," J. Bone Joint Surg. Am. 89:871-872, 2007.

(Continued)

Primary Examiner — Suzette J Gherbi
(74) Attorney, Agent, or Firm — Vinson & Elkins LLP (57) ABSTRACT

The present disclosure provides improved devices and methods to treat periprosthetic breast implant infections.

74 Claims, 5 Drawing Sheets